United States Patent [19]

Heimbrook et al.

[11] Patent Number: 4,943,561
[45] Date of Patent: Jul. 24, 1990

[54] GASTRIN RELEASING PEPTIDE ANTAGONIST

[75] Inventors: David C. Heimbrook, Ringoes, N.J.; Mark W. Riemen, Doylestown, Pa.; Allen Oliff, Gwynedd Valley, Pa.; Walfred S. Saari, Lansdale, Pa.

[73] Assignee: Merck & Co., Inc., Rahway, N.J.

[21] Appl. No.: 276,985

[22] Filed: Nov. 28, 1988

[51] Int. Cl.$^5$ .................... A61K 37/02; C07K 7/06
[52] U.S. Cl. ........................... 514/17; 514/16; 530/329
[58] Field of Search .................. 530/329; 514/16, 17

[56] References Cited

U.S. PATENT DOCUMENTS

| | | | |
|---|---|---|---|
| 4,476,051 | 10/1984 | Fujino et al. | 530/337 |
| 4,613,586 | 9/1986 | Barchas et al. | 530/326 |
| 4,636,490 | 1/1987 | Martinez et al. | 514/17 |

OTHER PUBLICATIONS

Broccardo et al., Br. J. Pharmac. 55:221–227 (1975).
Marki et al., Peptides 2, Suppl. 2:169–177 (1981).
Moody et al., Peptides 4 (5):683–686 (1983).
Jensen et al., Nature 309:61–63 (May 3, 1984).
Weber et al., J. Clin. Invest. 75:306–309 (1985).
Cuttitta et al., Nature, 316:823–826 (Aug. 29, 1985).
Corps et al., Biochem. J. 231:781–784 (1985).
Bepler et al., Cancer Research 47:2371–2375 (May 1, 1987).
Heinz-Erian et al., Am. J. Physiol. 252:0439–0442 (1987).
Coy et al., J. Biol. Chem. 263(11):5056–5060 (1988).
Heimbrook et al., J. Biol. Chem. 263(15):7016–7019 (1988).

Primary Examiner—Lester L. Lee
Attorney, Agent, or Firm—Donald J. Perrella; Hesna J. Pfeiffer

[57] ABSTRACT

Small cell lung carcinoma (SCLC) cells contain gastrin releasing peptide (GRP) receptors. The response of the cells to GRP is rapid growth. We have found a group of peptide derivatives that act as GRP antagonists by blocking the binding of GRP to its receptor thereby inhibiting the growth of cells that are sensitive to the growth promoting activity of GRP.

8 Claims, No Drawings

GASTRIN RELEASING PEPTIDE ANTAGONIST

BACKGROUND OF THE INVENTION

Gastrin releasing peptide (GRP), a 27-amino acid hormone, stimulates the growth of small cell lung carcinoma (SCLC) cells in cell culture. Antibodies directed against GRP block the growth of SCLC cells in nude mice.

DISCLOSURE STATEMENT

Broccardo et al., Br. J. Pharmac. 55:221-227 (1975), compare the pharmacological activity of two natural bombesin-like peptides and 25 related synthetic peptides to that of bombesin.

Marki et al., Peptides 2, Suppl. 2:169-177 (1981), disclose structure activity relationship of 26 peptide analogs of bombesin and GRP. The minimal essential residues required for full potency of bombesin-like effects is represented by an acetylated C-terminal 8-peptide fragment wherein position 7 can be substituted by alanine, histidine, glutamine or D-glutamine. Modification of the tryptophan [8] and histidine [12] residues by alanine abolished the biological potency of these peptides. A blocked N-terminus is necessary for maximum response.

Moody et al., Peptides 4 (5):683-686 (1983), disclose the presence of high concentrations of bombesin-like peptides and receptors in small cell lung cancer (SCLC) cells and suggest that bombesin may function as an important regulatory agent in human SCLC.

Jensen et al., Nature 309:61-63 (3 May 1984), disclose that a substance P analog is also a bombesin receptor antagonist.

Weber et al., J. Clin. Invest. 75:306-309 (1985), disclose that the mitogenicity of gastrin releasing peptide (GRP) resides in its carboxy terminal fragment, designated GRP 14-27, which is partly homologous to bombesin. The authors speculate that GRP or a closely related small peptide may be acting as an autocrine growth factor for SCLC cells.

Cuttitta et al., Nature, 316:823-826 (29 Aug. 1985), disclose that a monoclonal antibody to bombesin blocks the binding of the hormone to cellular receptors and inhibits the clonal growth of SCLC in vitro and the growth of SCLC xenografts in vivo demonstrating that bombesin-like peptides can function as autocrine growth factors for human SCLC.

Corps et al., Biochem. J. 231:781-784 (1985), disclose that an analog of substance P inhibits the stimulation of DNA synthesis induced in Swiss 3T3 cells by bombesin.

Bepler et al., Cancer Research 47:2371-2375 (1 May 1987), disclose that the undecapeptide physalaemin inhibits the clonal and mass culture growth of SCLC cell lines at picomolar concentrations.

Heinz-Erian et al., Am. J. Physiol. 252: G439-G442 (1987), disclosed that [D-Phe$^{12}$]analogs of bombesin are the only bombesin receptor antagonists identified to date that interact only with the bombesin receptor.

Coy et al., J. Biol. Chem. 263 (11):5056-5060 (1988), disclose [Leu $^{14}$]bombesin analogs wherein CONH peptide bond groups in the C-terminal octapeptide region were replaced by CH$_2$NH groups. One of them, [Leu$^{13}$-ψ-CH$_2$NH-Leu$^{14}$]bombesin inhibited bombesin stimulated growth of murine Swiss 3T3 fibroblast cells.

Heimbrook et al., J. Biol. Chem. 263 (15):7016-7019 (1988), disclose GRP-20-27, N-acetyl-GRP-21-27, N acetyl-GRP-22-27, and N-acetyl-GRP-23-27. All were less potent in binding inhibition and thymidine uptake assays than N-acetyl-GRP-20 27.

OBJECTS OF THE INVENTION

It is an object of the present invention to provide peptide derivatives that act as antagonists of GRP. Another object is to provide peptide derivatives having greater potency than those heretofore known. A further object is to provide a method of treating SCLC by administering a peptide derivative of the present invention. Another object is to provide methods for preparing these peptide derivatives. Yet another object is to provide peptide derivatives that are more readily synthesized than those heretofore known. These and other objects of the present invention will be apparent from the following description.

SUMMARY OF THE INVENTION

A series of peptide derivatives have been found which are GRP antagonists and which suppress GRP-stimulated mitogenesis in Swiss 3T3 cells.

The peptide derivatives of the present invention have the following formula:

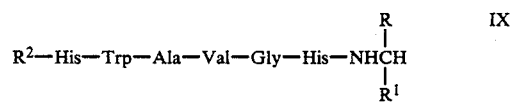

wherein R$^2$ is alkylacyl, alkylsulfonyl or alkoxy carbonyl, R and R$^1$ are the same or independently an alkyl or alkenyl group of from 1 to 8 carbon atoms, or an aryl alkyl group, wherein the alkyl, alkenyl and aromatic groups are optionally substituted with alkyl of from 1 to 3 carbon atoms, wherein the carbon containing R and R$^1$ is in either the R or S configuration and wherein any one optically active amino acid may be substituted by its D-isomer, or glycine may be substituted by Ala or D-Ala.

DETAILED DESCRIPTION OF THE INVENTION

The activity of the peptide derivatives of the present invention as GRP antagonists was determined in competitive binding assays with a radio-active GRP derivative. Swiss 3T3 fibroblasts were used in these tests as the source of GRP receptor. Because these cells respond to GRP binding with a rapid increase in DNA synthesis, compounds that bind to the GRP receptor can also be tested for their ability to stimulate DNA synthesis. New DNA synthesis is one of the early steps in cell division and is widely accepted as a measure of mitogenicity or cell growth. Compounds which bind to the receptor and do not stimulate growth are then tested for their ability to block GRP stimulated DNA synthesis. Compounds which block DNA synthesis are mitogenic antagonists. The efficacy of these antagonists against the GRP receptor on SCLC cells was demonstrated by measuring inhibition of GRP dependent calcium release in these cells.

The peptidyl moiety of the peptide derivatives present invention can be synthesized from their constituent amino acids by conventional peptide synthesi-s techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology"2, Chapter 1, Academic Press, 1980. The teachings of these works are hereby incorporated by reference.

The compounds of the present invention are prepared by reacting an acylated pentapeptide of the formula $R^2$ His-Trp-Ala-Val-Gly (or an analog wherein any one optically active amino acid optionally is substituted by its D-isomer, and glycine optionally is substituted by Ala or D-Ala), wherein $R^2$ has the same meaning as previously defined, with a histidine amide of the formula

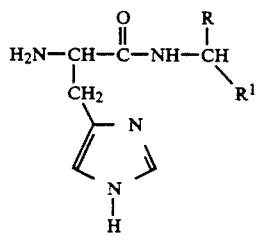   VIII

Optically active starting amino compounds of the present invention are prepared by resolution of the racemic amines using standard resolution methods or alternatively are prepared from optically active precursors using procedures which maintain their optical integrity. In the latter case an optically active aldehyde of the formula

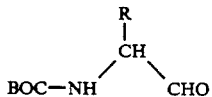   I is reacted with a phosphonium salt of the formula $\phi_3CP^+CH_2R^3Br^-$ II, wherein $R^3$ is an alkyl or aralkyl group. This reaction takes place under conditions suitable for Wittig reactions, e.g., in the presence of a base such as an alkyl lithium compound, for example n-butyl lithium; an alkali metal hydride, for example, NaH or KH; an alkali metal amide, for example, lithium diethyl amide (LDA); or an alkali metal hexamethyldisilazane, for example, potassium hexamethyldisilazane. The reaction takes place in the presence of a polar solvent such as an ether, for example, ethyl ether; or tetrahydrofuran (THF) or an alkyl sulfoxide, for example, dimethylsulfoxide (DMSO). The reaction takes place at about room temperature, typically at from about 20 to about 25° C. for a time period of from about 3 to about 24 hours. The reaction product is the unsaturated adduct of the formula

   III

Removal of the BOC protective group of III affords optically active alkenyl amines of formula

   IV

The unsaturated adduct of formula III may be catalytically hydrogenated to yield the saturated alkane of the formula

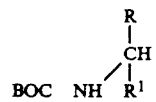   V

The hydrogenation takes place under any suitable conditions either at atmosphere pressure or above, in the presence of a catalyst such as, for example, Pd, PdO, Pt, or PtO₂, in a polar solvent such as an alcohol, for example, ethyl alcohol; an ester, for example, ethylacetate; or a furan, for example, THF. The hydrogenation takes place at about room temperature until 1 molar equivalent of H₂ has been absorbed.

Following hydrogenation, the saturated compound is recovered and the amino group is liberated by removal of the BOC protecting group to yield amines of the formula

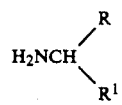   VI

Compounds of formula VI in which R and $R^1$ are identical may also be prepared from the corresponding ketone by reductive amination with a borohydride, for example sodium borohydride or sodium cyanoborohydride or by reduction of the corresponding oxime under catalytic hydrogenation conditions or with metal hydrides such as lithium aluminum hydride in solvents such as diethyl ether or tetrahydrofuran.

Compounds of formula IV or VI are then reacted with approximately an equimolar quantity of di-BOC-histidine in the presence of approximately an equimolar quantity of isobutyloxycarbonyl chloride, and approximately an equimolar quantity of N-methylmorpholine in ethyl acetate. The reaction takes place at temperatures of from about 0° C. to about 60° C. for a time period of from about 1 hour to about 24 hours to yield the adduct of di-BOC-histidine of formula VII.

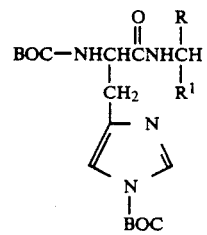   VII

This adduct is then deprotected under the usual acidic conditions and reacted with an acetylated pentapeptide of the formula $R^2$-His-Trp-Ala-Val-Gly (or an analog wherein any one optically active amino acid optionally is substituted by its D-isomer or wherein glycine optionally is substituted by Ala or-D Ala) to yield the compounds of formula IX or an analog wherein any one optically active amino acid optionally is substituted by its D-isomer, or wherein glycine optionally is substituted by Ala or D-Ala.

Known peptide antagonists of GRp are based on the structure of bombesin, a GRP analog containing 14 amino acids, or substance P, which contains 11 amino acids. The size of these antagonists are such that pharmacokinetic problems may be encountered. In addition, antagonists based on substance P show cross-reactivity with the substance P receptor.

Current chemotherapeutic agents for the treatment of SCLC are poorly effective. The treatment of SCLC by inhibiting the binding of GRP to its receptor offers advantages over conventional chemotherapy. First, use of a peptide derivative as an antagonist is intended to avoid the gross toxic side affects of conventional chemotherapy. In addition, receptor antagonists do not need to enter the cell to be effective.

The peptide derivatives of the present invention are effective in inhibiting the growth of cells that are sensitive to the growth promoting activity of GRP.

The following procedures were employed in determining the activity of the peptide derivatives of the present invention.

Procedure A

Binding Inhibition Studies

Swiss 3T3 cells, obtained from Dr. K. Brown (Institute of Animal Physiology, Cambridge, U.K.), were grown to confluency in Costar 12 -well plates containing DMEM (Gibco) supplemented with 10% fetal bovine serum, 2 mM glutamine and 1% penicillin-streptomycin. The cells were washed twice with binding buffer [1:1 DMEM:Waymouths MB752/1 medium, plus 1 mg/ml BSA (Fraction V, Calbiochem)]. The antagonist was dissolved in 10 mM HCl, and diluted to the appropriate concentration in binding buffer. The antagonist was then added to the cells, followed by [$^3$H Phe$^{15}$]GRP15-27 at a final concentration of 3 nM. After 60 minutes incubation at 15° C., the supernatant liquid was removed and the cell monolayer rinsed four times with washing buffer (150 mM NaCl, 20 mM Na$_2$HPO$_4$, 5mM KCl, 1.8 mM KH$_2$PO$_4$, 1 mg/ml BSA) The cells were then lysed with 1 ml/well of lysis buffer (1% Triton X-100, 0.1% BSA), and the solution was aspirated into scintillation vials for counting. Each data point was collected in triplicate.

Procedure B

Mitogenic Stimulation

Swiss 3T3 cells were grown in monolayer culture in 24 -well plates (Costar) in serum free DMEM for 48 hours, at which time the GRP or GRP homologue, and 23 nM $^3$H-thymidine were added. After an additional 48 hours, the cell monolayer was washed twice with PBS, and the cells were then removed with 1 ml 10x trypsin containing 5 mM EDTA. The cells were harvested with a Skatron filter apparatus, and the filters counted in a scintillation counter.

Procedure C

Mitogenesis Inhibition

Swiss 3T3 cells were grown in monolayer culture in 24 -well plates (Costar) in serum free DMEM for 48 hours, at which time the GRP or a GRP homologue. The antagonist and 23 nM $^3$H-thymidine were added. After an additional 48 hours, the cell monolayer was washed twice with PBS, and the cells were then removed with 1 ml 10x trypsin containing 5 mM EDTA. The cells were harvested with a Skatron filter apparatus, and the filters counted in a scintillation counter.

Procedure D

Stimulation of Ca$^{2+}$ Release in SCLC

Following the procedure of Heikkila et al., J. Biol. Chem. 262 16456 (1987), approximately $1 \times 10^8$ H345 SCLC cells, maintained in RPMI 1640 (Ro) medium supplemented with selenium, insulin, and transferring, were harvested by settling and washed with Ro. They were then resuspended in 2 ml Ro, to which 1.2 nmol Fura-2/AM per $10^6$ cells was added. After a 15 minute incubation at 37° C., the cells were diluted to 10 ml with Ro and incubated for 1 hour at 37° C., the cells were then centrifuged and resuspended in HEPES saline (140 mM NaCl, 5mM KCl, 5mM glucose, lmM CaCl$_2$, 1 mM MgCl$_2$, 20mM HEPES, pH 7.4) at a density of $2.5-5 \times 10^6$ cells/ml. The cells were kept on ice for up to 2 hours before being used. Ca$^{2+}$ measurements were performed at 37° C. in an Aminco SPF-500 fluorimeter. The excitation wavelength was 340 nm, the emission wavelength 510 nm. Two ml of cell suspension was periodically resuspended in a 3 ml plastic cuvette. They were equilibrated at 37° for at least 5 minutes before data was collected. After a stable baseline was established, a mixture of the compound of interest and 100 nM GRP was added, and data was collected for approximately 5 minutes. At that time, a challenge dose of GRP was added, and data was collected for an additional 5 minutes. The cells were then lysed with 4 μl 10% Triton X-100 to measure peak fluorescence. Baseline fluorescence was measured after the subsequent addition of 40 μl 2M Tris (pH 9.5) and 64 μl 0.2 M EGTA.

The results obtained with representative antagonists of the present invention are shown in the following Table.

TABLE I

| Example | Procedure (IC$_{50}$) | | | |
|---|---|---|---|---|
| | A | B | C | D |
| 1(R) | 2 nM | NR | 4 nM | 200 nM |
| 1(S) | 17 nM | NR | 22 nM | NT |
| 2(S) | 11 nM | NT | NT | NT |
| 3(R) | 15 nM | NR | 35 nM | NT |
| 4(R) | 3 nM | NR | 2 nM | NT |
| 5(R) | 2 nM | NT | NT | NT |
| 6 | 2 nM | NR | 2 nM | NT |

NR — No response to >300 nM
NT —Not Tested

The following examples illustrate the present invention without, however, limiting the same thereto. Unless indicated otherwise, all optically active amino acids have L-configuration. All temperatures are expressed in degrees Celsius.

EXAMPLE 1

Step 1. (S)-2-Methyl-4 -(tert. butoxycarbonylamino)-5-nonene

Potassium hexamethyldisilazane (10.8 mL of a 1.85M solution in THF, 20 mmol) was added over 15 minutes to a stirred mixture of n-butyl triphenyl-phosphonium bromide (7.99 g., 20 mmol) and THF (75 mL) at 0°. After addition was complete, the mixture was stirred at 0° for 30 minutes and then a solution of (S)-2-methyl-4-(tert. butoxycarbonylamino) pentanal (2.04 g, 9.48 mmol) in toluene (10 mL) was added over 15 minutes. The reaction mixture was stirred at 0° for 30 minutes, 20°-25° for 30 minutes and then at 40° for 18 hours. Methanol (1 mL) then H₂O (5 mL) were added and solvents removed under reduced pressure at 40°. The residue was partitioned between ethyl acetate and a dilute solution of Rochelle's salt. The ethyl acetate extract was washed with brine, dried (Na₂SO₄), filtered and concentrated. Flash chromatography of the residue over silica gel and elution with 10% ethyl acetate 90% hexane gave 2.10 g of product.

Step 2. (R)-2 -Methyl-4 -(tert. butoxycarbonylamino) nonene.

A solution of (S)-2 -methyl-4 -(tert butoxycarbonylamino)-5 -nonene (2.0 g) in absolute ethanol (75 mL) was hydrogenated over a 5% palladium on carbon catalyst (1.0 g) at 20°-25° and an initial pressure of 34 psi in a Paar apparatus. After one equivalent of hydrogen had been taken up (1 hour), the mixture was filtered and then concentrated under reduced pressure to give 1.78 g of product.

Step 3. (R)-2-Methyl-4 -aminononane Hydrochloride

A solution of (S)-2 -methyl-4 -(tert. butoxycarbonylamino)nonane (1.7 g) in ethyl acetate (50 mL) was cooled in an ice bath under a drierite tube and saturated with anhydrous hydrogen chloride gas for 7 minutes. After stirring at 0° for 1 hour and then at room temperature for one hour, solvent was removed under reduced pressure and the solid residue recrystallezed from hexane-n-butyl chloride to give the amine hydrochloride (0.52 g), mp 142°-144° soften at 135°.

Step 4. N-[(R)-2 -Methyl-4-nonanyl]NαN$_{im}$,-Bis-BOC-(S)-histidineamide

A mixture of Nα,Nim-bis-BOC-histidine ethyl acetate solvate (1.92 g, 5.0 mmol), 4 -methylmorpholine (0.55 mL, 5.0 mmol) and isobutyl chloroformate (0.65 mL, 5.0 mmol) in ethyl acetate (50 mL) was stirred in an ice bath under N₂ for 15 minutes. A solution of (R)-2-methyl-4-aminononane hydrochloride (0.97 g, 5.0 mmol) in ethyl acetate (10 mL) followed by 4 methylmorpholine (0.55 mL, 5.0 mmol) were added and the reaction stirred at room temperature for 20 hours. After washing with 10% citric acid, brine, saturated NaHCO₃ solution and brine, the ethyl acetate extract was dried (Na₂SO₄), filtered and concentrated under reduced pressure. The residue was flash chromatographed over silica gel. Elution with a mixture of 2% methanol and 98% chloroform afforded pure BOC protected histidineamide.

Step 5. N-[(R)-2-Methyl-4 -nonanyl](S) -Histidineamide

A solution of the BOC-protected amide from Step 4 (0.90 g) in ethyl acetate (25 mL) was cooled in an ice bath and saturated with HCl gas for 5 minutes. After stirring at ice bath temperature for 1 hour and then at room temperature for 1 hour, solvent was removed under reduced pressure and the residue dried to give the deprotected amide hydrogen chloride salt.

Step 6. Preparation of Ac-His-Trp-Ala-Val-Gly

This peptide was prepared by a standard solid phase procedure beginning with BOC-glycyl resin with additional amino acids added with DCC coupling.

Step 7.

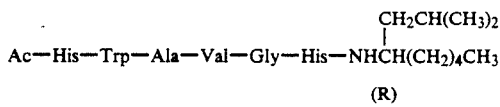

Ac—His—Trp—Ala—Val—Gly—His—NHCH(CH₂)₄CH₃

(R)

A solution of the histidine amide hydrogen chloride salt from Step 5 (16 mg), the peptide of Step 6 (23 mg), 1-hydroxybenzotriazole (5.4 mg), triethylamine (14 μL) and dicyclohexylcarbodiimide (7.2 mg) in DMF (3 mL) was stirred at room temperature under N₂ for 20 hours. After concentrating under reduced pressure, the residue was mixed with distilled water and filtered. The aqueous extract was washed with ethyl acetate two times, filtered and lyophilized to give a white powder. This product was purified by preparative HPLC to give the product as a white solid.

EXAMPLE 2

Step 1. (S)-2-methyl-4-amino-5-nonene Hydrochloride

A solution of (S)-2-methyl-4-(tert.butoxy carbonylamino)-5 -nonene (1.0 g) in ethyl acetate (50 mL) was cooled in an ice bath under a drierite tube and saturated with hydrous hydrogen chloride gas for 8 minutes. After stirring in the ice bath for 45 minutes, solvent was removed under reduced pressure to give the deprotected alkenylamine hydrochloride.

Step 2. N-[(S)-2-Methyl-5 -nonen-4-yl]N₆₀,N$_{im}$-Bis-Boc-(S)-histidineamide A mixture of N₆₀,N$_{im}$-bis-BOC-histidine ethyl acetate solvate (1.27 g, 3.29 mmol), 4 -methylmorpholine (0.36 mL, 3.29 mmol) and isobutylchloroformate (0.43 mL, 3.29 mmol) in ethyl acetate was stirred in an ice bath under N₂ for 15 minutes. (S)-2 Methyl-4-amino-5 -nonene hydrochloride (0.63 g, 3.29 mmol) was added followed by N-methylmorpholine (0.36 mL, 3.29 mmol) and the reaction mixture stirred at room temperature for 20 hours. After washing with 10% citric acid, brine, saturated NaHCO₃ solution and brine, the ethyl acetate extract was dried (Na₂SO₄), filtered and concentrated under reduced pressure. The residue was flash chromatographed over silica gel. Elution with a mixture of 2% isopropanol and 98% chloroform gave 0.94 g of product.

Recrystallization from ethyl acetate-hexane gave analytically pure product, mp 85.0°-90.0°.

Step 3. N-[(S)-2-Methyl-5 -nonen-4-yl]-(S)-Histidine-amide

A solution of the BOC-protected amide from Step 2 (0.80 g) in ethyl acetate (50 mL) was cooled in an ice bath and saturated with HCl gas for 7 minutes. After stirring at ice bath temperature for 1 hour, solvent was removed under reduced pressure and the residue dried to give the deprotected amide HCl salt.

Step 4.

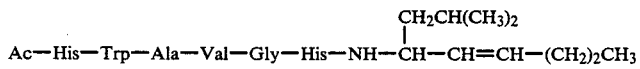

A solution of the histidine amide from Step 3 (26 mg), the peptide of Step 6, Example 1 (28 mg), 1 hydroxybenzotriazole (8.3 mg), triethylamine (30 μL) and dicyclohexylcarbodiimide (14.8 mg) in DMF (10 mL) was stirred at room temperature under $N_2$ for 20 hours. After concentrating under reduced pressure, the residue was triturated with distilled water and filtered. The aqueous extract was lyophilized to give a white powder. This product was purified by preparative HPLC to give the product as a white solid.

EXAMPLE 3

Step 1. His-Trp-Ala-Val-Gly

This peptide was prepared by a standard solid phase procedure beginning with BOC-glycyl resin with additional amino acids added with DCC coupling. It was purified by preparative HPLC.

Step 2. $CH_3SO_2NH$ His-Trp Ala-Val-Gly

Reaction of the peptide from Step 1 with methanesulfonyl chloride in DMF in the presence of triethylamine affords the mesyl derivative.

Step 3.

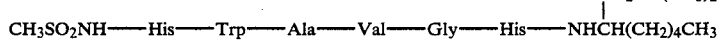

Coupling of the acid from Step 2 with the histidine amide of Step 5, Example 1 following the procedure of Step 7, Example 1 gives the mesyl derivative of this Example.

EXAMPLE 4

Step 1.

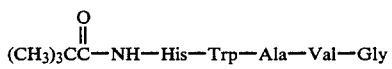

This peptide was prepared by the method of Step 6, Example 1 by substituting pivalic anhydride for acetic anhydride.

Step 2.

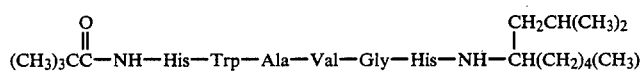

Coupling of the acid from Step 1 with the histidine amide of Step 5, Example 1 following the procedure of Step 7, Example 1 gave the pivaloyl derivative of this Example.

EXAMPLE 5

Step 1.

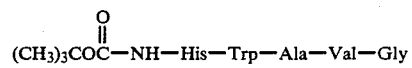

Reaction of the peptide from Step 1, Example 3 with di (tert. butyl) dicarbonate in DMF affords this BOC peptide.

Step 2.

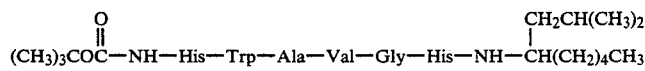

Coupling of the acid from Step 1 with the histidine amide of Step 5, Example 1 following the procedure of Step 7, Example 1 gives the BOC derivative of this Example.

EXAMPLE 6

Step 1. 2,6-Dimethyl-4-aminoheptane Hydrochloride

A solution of 2,6-dimethyl-4-heptanone (2.84 g, 20 mmol), ammonium acetate (15.4 g, 200 mmol) and sodium cyanoborohydride (0.93 g, 14 mmol) in methanol (75 mL) was stirred at room temperature for 20 hours. After cooling in an ice bath, the reaction mixture was acidified with concentrated HCl and concentrated under reduced pressure at 35°. The residue was partitioned between ethyl ether and water and the aqueous portion removed and made basic with 40% NaOH solution. Product was extracted into ethyl ether which was then washed with brine, dried ($Na_2SO_4$), filtered and concentrated to 1.22 g of product. Conversion to the HCl salt and recrystallation from MeOH-EtOAc gave 1.04 of pure HCl salt, mp 248°–50° dec.

Step 2.

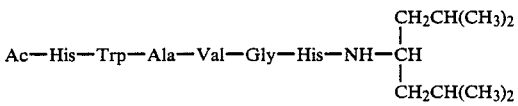

This peptide was prepared by following the procedures of Steps 4–7 of Example 1 with the amine of Step 1 of this Example replacing (R)-2-methyl-4-aminononane hydrochloride.

What is claimed is:

1. A compound having the formula

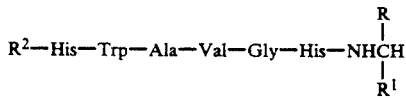

wherein $R^2$ is alkylacyl, alkylsulfonyl or alkoxy carbonyl, R and $R^1$ are the same or independently an alkyl or alkenyl group of from 1 to 8 carbon atoms, or an aryl alkyl group, wherein the alkyl, alkenyl and aromatic groups are optionally substituted with alkyl of from 1 to 3 carbon atoms, wherein the carbon containing R and $R^1$ is in either the R or S configuration and wherein any one optically active amino acid may be substituted by its D-isomer, or glycine may be substituted by Ala or D-Ala.

2. A compound of claim 1 wherein $R^2$ is acetyl, $CH_3SO_2$,

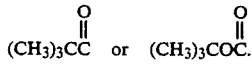

3. A compound of claim 1 wherein R is $CH_2CH(CH_3)_2$.

4. A compound of claim 1 wherein R is $CH_2CH(CH_3)_2$ and $R^1$ is $(CH_2)_nCH_3$ wherein n is 2, 3 or 4.

5. A compound of claim 1 wherein $R^2$ is

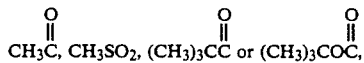

and R is $CH_2CH(CH_3)_2$, and $R^1$ is $CH_2CH(CH_3)_2$ or $(CH_2)CH_{3n}$ wherein n is 2, 3 or 4.

6. A compound of claim 1 selected from
(1) $R^2$ is acetyl, R is $CH_2CH(CH_3)_2$ and $R^1$ is $(CH_2)_4CH_3$,
(2) $R^2$ is acetyl, R is $CH_2CH(CH_3)_2$ and $R^1$ is $CH=CH(CH_2)_2CH_3$,
(3) $R^2$ is $CH_3SO_2$, R is $CH_2CH(CH_3)_2$ and $R^1$ is $(CH_2)_4CH_3$,
(4) $R^2$ is $$(CH)_3C\overset{O}{\underset{\|}{C}},$$

R is $CH_2CH(CH_3)_2$ and $R^1$ is $(CH_2)_4CH_3$,
(5) $R^2$ is

R is $CH_2CH(CH_3)_2$ and $R^1$ is $(CH_2)_4CH_3$, or
(6) $R^2$ is acetyl, R is $CH_2CH(CH_3)_2$ and $R^1$ is $CH_2CH(CH_3)_2$.

7. A composition comprising a compound of claim 1 and a pharmaceutically acceptable carrier, the composition being effective to inhibit the growth of cells that are sensitive to the growth promoting activity of GRP.

8. A method of inhibiting the growth of cells that are sensitive to the growth promoting activity of GRP which comprises treating the cells with a compound of claim 1 in an amount effective to antagonize the growth promoting activity of GRP.

* * * * *